United States Patent [19]

Armstrong

[11] Patent Number: 5,709,710
[45] Date of Patent: Jan. 20, 1998

[54] IMPLANTABLE CARDIOVERTER/ DEFIBRILLATOR WITH ADAPTIVE SHOCK COUPLING INTERVAL AND METHOD

[76] Inventor: Randolph Kerry Armstrong, 4231 King Cotton La., Missouri City, Tex. 77459

[21] Appl. No.: 435,404

[22] Filed: May 10, 1995

[51] Int. Cl.⁶ .................................. A61N 1/39
[52] U.S. Cl. ........................................ 607/5
[58] Field of Search ........................ 607/4, 5, 14

[56] References Cited

U.S. PATENT DOCUMENTS

| | | |
|---|---|---|
| 4,800,883 | 1/1989 | Winstrom . |
| 4,830,006 | 5/1989 | Haluska et al. . |
| 4,860,749 | 8/1989 | Lehmann . |
| 4,865,036 | 9/1989 | Chirife . |
| 4,940,054 | 7/1990 | Grevis et al. . |
| 4,996,984 | 3/1991 | Sweeney . |
| 4,998,974 | 3/1991 | Aker .................. 607/4 |
| 5,105,810 | 4/1992 | Collins et al. . |
| 5,133,353 | 7/1992 | Hauser ................ 607/4 |
| 5,161,527 | 11/1992 | Nappholz et al. ...... 607/14 |
| 5,161,528 | 11/1992 | Sweeney . |
| 5,163,428 | 11/1992 | Pless . |
| 5,168,869 | 12/1992 | Chirife . |
| 5,183,040 | 2/1993 | Nappholz et al. . |
| 5,184,616 | 2/1993 | Weiss . |
| 5,188,105 | 2/1993 | Keimel . |
| 5,215,081 | 6/1993 | Ostroff . |
| 5,231,986 | 8/1993 | Bennett . |
| 5,235,976 | 8/1993 | Spinelli . |
| 5,257,621 | 11/1993 | Bardy et al. . |
| 5,275,621 | 1/1994 | Mehra . |
| 5,318,591 | 6/1994 | Causey, III et al. . |
| 5,370,667 | 12/1994 | Alt . |
| 5,383,909 | 1/1995 | Keimel ................ 607/7 |

FOREIGN PATENT DOCUMENTS 908373  2/1982  U.S.S.R. .

OTHER PUBLICATIONS

Synchronous Intracardiac Cardioversion, Douglas P. Zipes, James Heger, William M. Miles, and Eric N. Prystowsky, from the Krannert Institute of Cardiology, Dept. of Medicine, Indiana University School of Medicine, Veterans Administration Hospital, Indianapolis, Indiana, May–Jun. 1984, Part II, vol. 7, pp. 522–533.

*Primary Examiner*—Jeffrey R. Jastrzab
*Attorney, Agent, or Firm*—Gunn & Associates, P.C.

[57] ABSTRACT

An implantable cardioverter/defibrillator with adaptive coupling interval modifies known cardioverter devices that have a set, though adjustable shock coupling interval. The cardioverter/defibrillator determines the time interval between events in the cardiac cycle, and calculates a coupling interval based upon the duration between these timed events. The adaptive coupling interval may be set at a desired percentage of the interval between events.

5 Claims, 2 Drawing Sheets

IMPLANTABLE CARDIOVERTER/ DEFIBRILLATOR WITH ADAPTIVE SHOCK COUPLING INTERVAL AND METHOD

FIELD OF THE INVENTION

The present invention relates generally to the field of heart cardioverter and defibrillator equipment. More specifically, the present invention relates to a special cardioverter/ defibrillator device which is suitable for use in implantable, automatic cardioversion and defibrillation systems and includes an adaptive shock coupling interval.

BACKGROUND OF THE INVENTION

Ventricular fibrillation is almost always fatal unless promptly arrested. It has long been known that the application of a high energy pulse to the heart is often particularly effective in arresting this otherwise fatal condition and in restoring the synchronous operation of the heart muscles.

Automatic, implantable fibrillation sensors and defibrillation pulse generators are known in the art. See, for example, U.S. Pat. Nos. 4,800,883 to Winstrom and 4,830,006 to Haluska, et al. The shocks delivered for cardioversion and defibrillation may be identical, but the medical condition giving rise to the need for one or the other is fundamentally different. Cardioversion refers to the method of terminating a tachycardia, i.e., rapid heartbeat, while defibrillation is the method of terminating fibrillation, and both tachycardia and fibrillation are arrhythmias.

Zipes et al., in Synchronous Intracardiac Cardioversion, PACE, vol. 7, pp. 522 et seq., explore the impact of synchronization of various energies of pulses on cardioversion. The experiments described in this article placed pulses at 5-20 msec. resolution steps through the tachycardia cycle. Further, the experimentation was carried out with fixed coupling intervals, i.e., the time from a ventricular event to the imposition of the synchronized shock. While adjustable, this coupling interval was fixed within the instrument, and did not depend on the rate of the irregular heartbeat or tachycardia. However, triggering the pulse at a fixed time interval after a sensed ventricular event may not provide the optimum point in the cycle to effectuate cardioversion, as shown in Zipes et al.

Thus, there remains a need for an implantable cardioverter/defibrillator that triggers the cardioversion pulse at a point in the ventricular cycle that is adaptive to the rate of the irregular heartbeat.

SUMMARY OF THE INVENTION

The present invention solves this problem of the prior art by providing an implantable cardioverter/defibrillator with adaptive coupling interval. The invention modifies known cardioverter devices that have a set, though adjustable shock coupling interval. However, the cardioverter/defibrillator determines the time interval between events in the cardiac cycle, and calculates a coupling interval based upon the duration between these timed events. For example, if a heart is beating at a rate of 300 msec. between events in the cycle, and the adaptive coupling interval has been programmed in the device at 30%, then the actual coupling interval from the next event to the imposition of the cardioverter pulse is 90 msec. The adaptive coupling interval may be set at a desired percentage of the interval between events.

Such an adaptive coupling interval increases the likelihood of cardioversion and defibrillation. This invention reduces the cardioversion threshold and the need for subsequent shocks or additional therapies. It also reduces the likelihood of tachycardia acceleration and patient discomfort.

These and other features and advantages of the present invention will be immediately apparent to those of skill in the art from a review of the following detailed description along with the accompanying drawings.

DETAILED DESCRIPTION OF A PREFERRED EMBODIMENT

Figure 1:
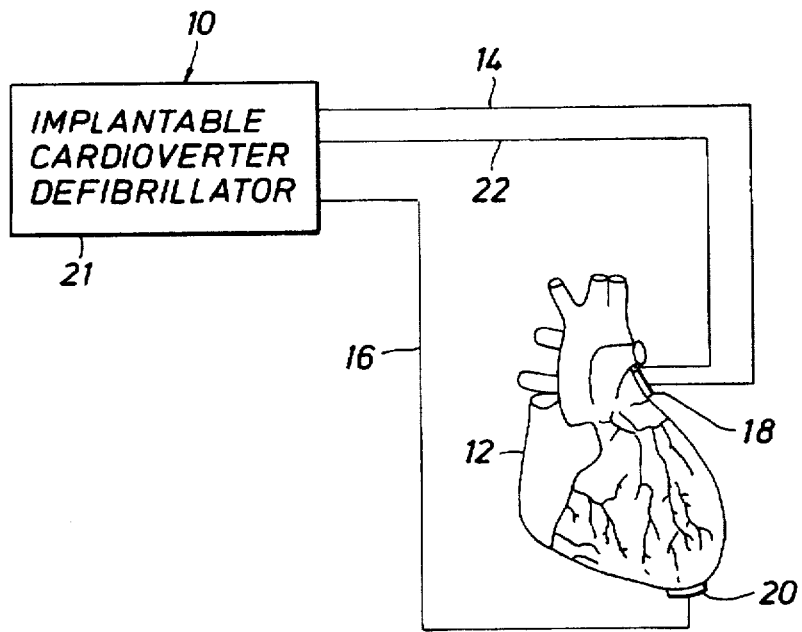
FIG. 1 is a general block diagram of a prior art system for the application of a high energy pulse to a heart.

FIG. 1 depicts a known arrangement for a device which carries out cardioversion or defibrillation. An implantable cardioverter/defibrillator (ICD) 10 is coupled to a human heart 12. A pair of leads 14 and 16 connect the ICD 10 to the heart at their respective conductive patches 18 and 20. The leads 14 and 16 conduct the high energy pulse to the heart and may be referred to as cardioversion/defibrillation leads or shock leads. It is well known that the conductors of leads 14 and 16 may be included in a single lead, or they may be combined with other additional leads. Further, the ICD containment can 21 may itself be used as one of the leads, such as the shock lead.

A rate sensing lead 22 also couples the ICD to the heart. The rate sensing lead monitors the electrical activity in the heart. The lead 22 provides an electrical signal from the heart 12 to the ICD to indicate the rate of the cardiac cycle. The rate sensing lead will, most often, have both poles of the sensing electrodes on a single lead.

Figure 2:
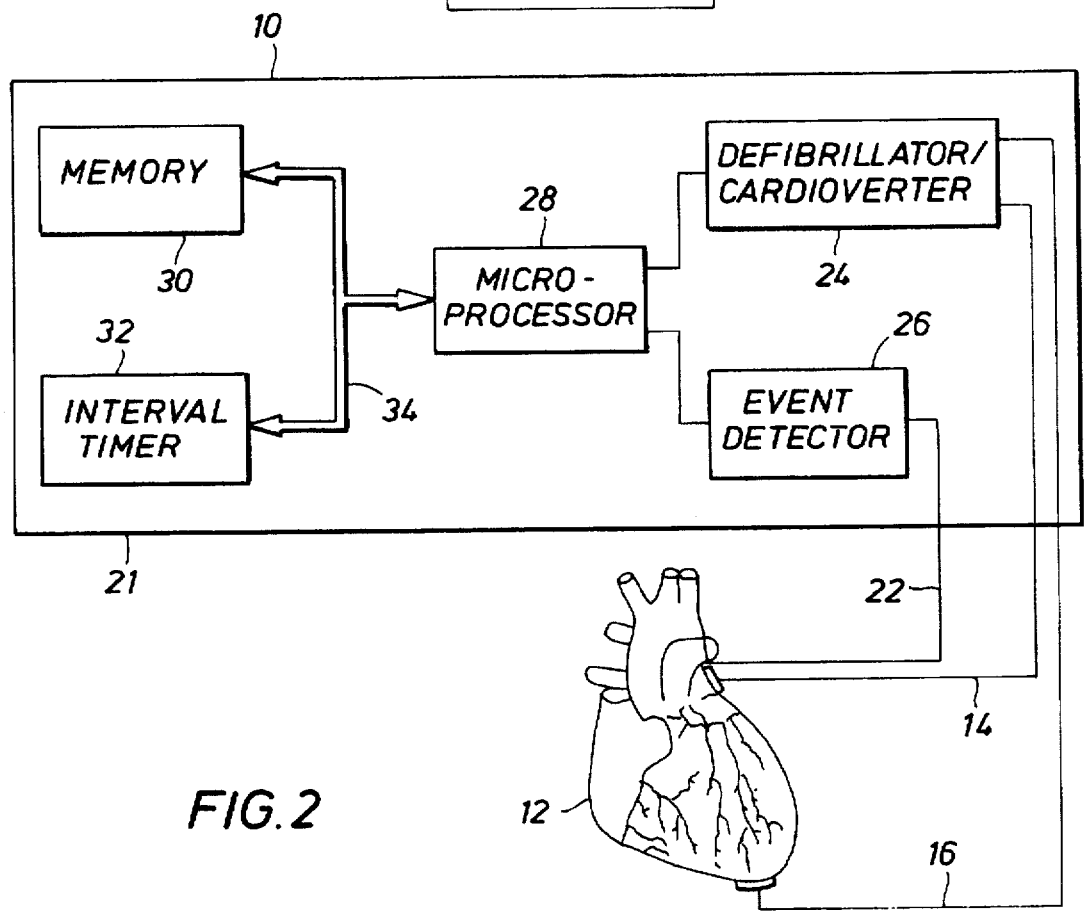
FIG. 2 is a block diagram showing the various circuit components that cooperate to provide the adaptive shock coupling interval to a heart.

FIG. 2 depicts the arrangement of the various components within the ICD 10 and how it is preferably coupled to the heart 12. As before, cardioversion leads 14 and 16 couple the shock pulse to the heart 12, and a rate sensing lead 22 carries the cardiac rate signal back to the ICD 10.

The ICD 10 comprises a defibrillator/cardioverter 24 which provides the shock pulse over the leads 14 and 16, an event detector 26 which receives the cardiac rate signal over the rate sensing lead 22, a central processing unit such as a microprocessor 28 which provides overall control of the ICD 10, a memory 30 which may include random access and/or read only memory, and an interval timer 32. Among other parameters, the memory 30 stores the selected (programmed) adaptive coupling interval, stated as a percentage of the time duration between cardiac events.

The memory 30 and the interval timer 32 are coupled to the microprocessor 28 via a bus 34 for multi-bit, digital communication with the microprocessor 28. The interval timer 32, such as a high-speed clock, times the duration between events, as detected by the event detector 26. This time duration, as provided by the interval timer 32, is used in the adaptive control of the present invention.

Figure 3:
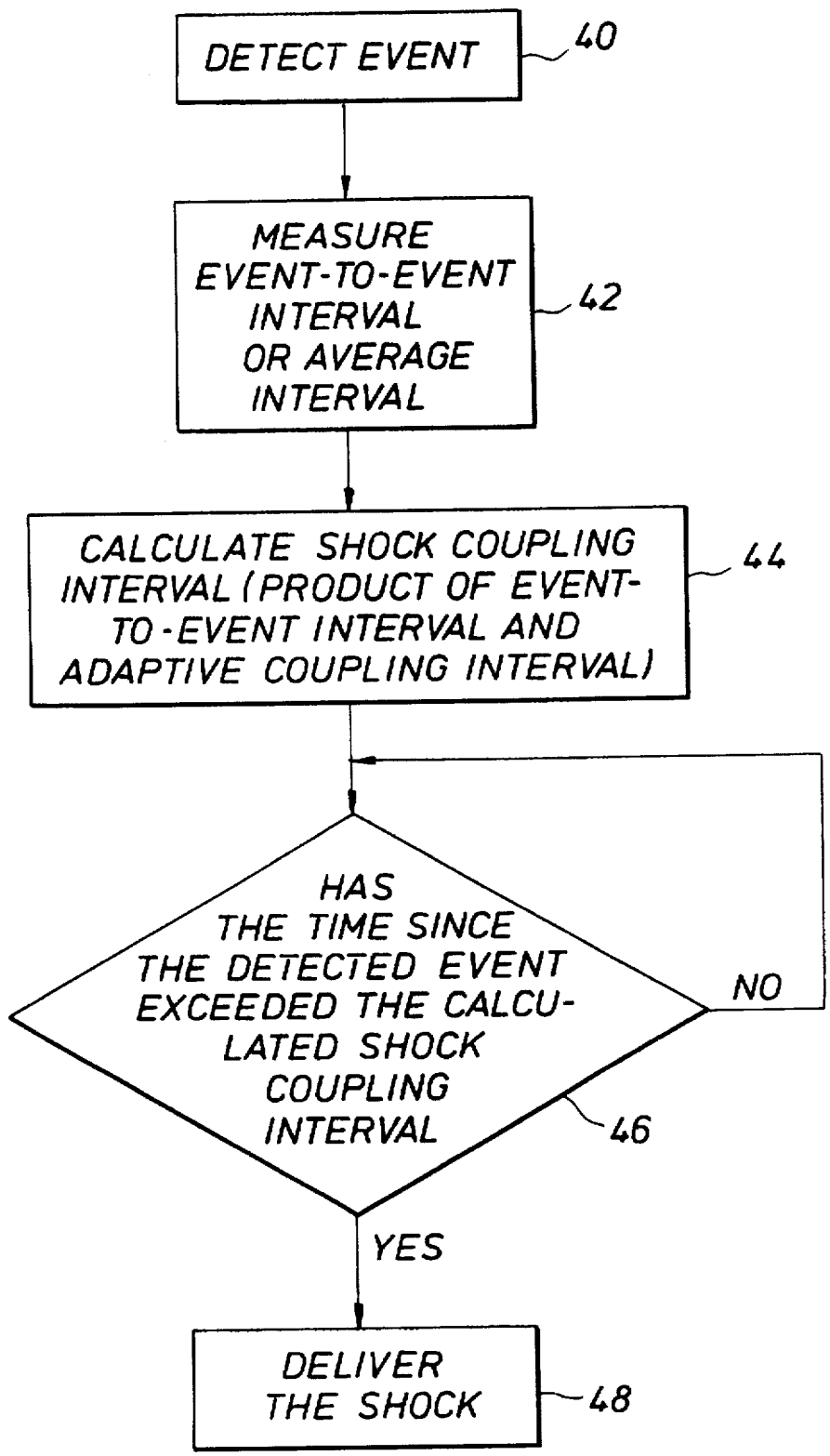
FIG. 3 is a logic flow diagram showing the logic programmed into a microprocessor within the device to provide the adaptive shock coupling interval.

FIG. 3 provides a logic flow diagram, carried out in the microprocessor 28, to use the detected event and the duration between events in the adaptive control of the present invention. The logic flow of FIG. 3 is executed whenever a cardioversion or defibrillation shock must be delivered and an adaptive shock coupling interval is desired.

In step 40, the event detector 26 detects an event, such as a ventricular event, in a manner known in the art. This may be accomplished with a threshold detector or other appropriate means.

When the next subsequent event is detected by the detector 26, step 42 measures the time interval between events. This time interval is provided over the bus 34 to the microprocessor. Step 42 may also be modified to provide the average duration over a number of measured intervals. The microprocessor then acquires the adaptive coupling interval stored in the memory 30 and calculates the shock coupling interval in step 44.

Step 46 monitors for the elapsed time of the calculated shock coupling interval from step 44. Until this time has elapsed, the microprocessor continues to loop to the beginning of step 46. Once this time has elapsed, the microprocessor 28 sends a command signal to the defibrillator/cardioverter 24 which delivers the shock in step 48.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

I claim:

1. A cardioverter/defibrillator having pulse carrying electrodes and a rate sensing electrode for connection to a heart, the cardioverter comprising:

a. a shock pulse source coupled to the pulse carrying electrodes;

b. an event detector coupled to the rate sensing electrode;

c. means for determining a time duration between events detected by the event detector;

d. means for storing a predetermined adaptive coupling interval; and e. central processor for calculating a shock coupling interval as a function of the determined time duration between events and the adaptive coupling interval, thereby triggering the shock pulse source based upon the calculated shock coupling interval to cardiovert the heart.

2. The cardioverter/defibrillator of claim 1 further comprising a containment to permit the implantation of the cardioverter/defibrillator.

3. The cardioverter/defibrillator of claim 1 wherein the pulse carrying electrode comprises a containment can encapsulating the cardioverter/defibrillator.

4. A cardioversion/defibrillation method comprising the steps of:

a. sensing a first cardiac event of a heart at a first time;

b. sensing a second, successive cardiac event of the heart at a second time;

c. determining the difference in time between the first time and the second time to define a time duration between the first and the second cardiac events, thereby determining a rate of the cardiac cycle of the heart;

d. storing an adaptive coupling interval in a memory;

e. calculating a shock coupling interval as a function of the time duration determined in step c. and the adaptive coupling interval; and f. triggering a shock pulse source at the shock coupling interval to thereby cardiovert the heart.

5. The method of claim 4 further comprising the steps of:

a. sensing a series of successive cardiac events at successive times;

b. determining differences in times between the successive cardiac events;

c. calculating the average of the differences in times; and d. defining the average as the time duration between cardiac events.

* * * * *